(12) United States Patent
Basu et al.

(10) Patent No.: US 10,058,293 B2
(45) Date of Patent: Aug. 28, 2018

(54) DETECTOR ASSEMBLIES AND METHODS FOR HELICAL CT SCANNING

(71) Applicant: Morpho Detection, LLC, Newark, CA (US)

(72) Inventors: Samit Kumar Basu, Fremont, CA (US); Seungseok Oh, Fremont, CA (US); Pedro Andres Garzon, Santa Clara, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 215 days.

(21) Appl. No.: 15/048,130

(22) Filed: Feb. 19, 2016

(65) Prior Publication Data
US 2017/0238886 A1 Aug. 24, 2017

(51) Int. Cl.
*A61B 6/00* (2006.01)
*A61B 6/03* (2006.01)
*A61B 6/02* (2006.01)

(52) U.S. Cl.
CPC ............ *A61B 6/4233* (2013.01); *A61B 6/027* (2013.01); *A61B 6/032* (2013.01); *A61B 6/4266* (2013.01)

(58) Field of Classification Search
CPC ........ G01N 23/00; G01N 23/046; A61B 6/00; A61B 6/02; A61B 6/027; A61B 6/03; A61B 6/032; A61B 6/4233; A61B 6/4266
USPC ........................................ 378/4, 15, 19, 901
See application file for complete search history.

(56) References Cited

U.S. PATENT DOCUMENTS

| | | |
|---|---|---|
| 6,823,044 B2 | 11/2004 | Rosner |
| 7,606,348 B2 | 10/2009 | Foland et al. |
| 7,606,349 B2 | 10/2009 | Oreper et al. |
| 7,792,239 B2 | 9/2010 | Nambu et al. |
| 7,831,012 B2 | 11/2010 | Foland et al. |
| 8,111,804 B2 | 2/2012 | Dafni et al. |
| 8,718,227 B2 | 5/2014 | Dafni |
| 8,873,705 B2 | 10/2014 | Konno et al. |
| 8,983,165 B2 | 3/2015 | Sun et al. |

(Continued)

FOREIGN PATENT DOCUMENTS

| | | |
|---|---|---|
| DE | 102014116595 A1 | 5/2015 |
| WO | 2013126649 A2 | 8/2013 |

OTHER PUBLICATIONS

Extended European Search Report, Application No. 17000258.8, dated Jun. 21, 2017, 7 pps.

(Continued)

*Primary Examiner* — Jurie Yun
(74) *Attorney, Agent, or Firm* — Armstrong Teasdale LLP

(57) ABSTRACT

A helical CT scanner for imaging an object is provided. The helical CT scanner includes an X-ray emitter configured to emit X-ray beams towards the object, and a detector array positioned opposite the X-ray emitter, the detector array including a plurality of discrete detector blocks arranged in a two-dimensional grid, each detector block including a plurality of pixels, wherein at least one first gap is defined between adjacent detector blocks in a first direction, and wherein at least one second gap is defined between adjacent detector blocks in a second direction. The helical CT scanner further includes a processing device communicatively coupled to said detector array, said processing device configured to reconstruct an image of the object based on image data acquired using said detector array.

20 Claims, 5 Drawing Sheets

(56) References Cited

U.S. PATENT DOCUMENTS

| | | |
|---|---|---|
| 9,069,092 B2 | 6/2015 | Oreper et al. |
| 9,076,563 B2 | 7/2015 | Ying |
| 9,389,320 B2 * | 7/2016 | Ogawa ................... A61B 6/14 |
| 2008/0056436 A1 | 3/2008 | Pack et al. |
| 2013/0016805 A1 | 1/2013 | Silver et al. |
| 2014/0010343 A1 | 1/2014 | Basu et al. |
| 2016/0025867 A1 | 1/2016 | Sun et al. |

OTHER PUBLICATIONS

Microtec—Goldeneye 300, printed Feb. 19, 2016, website—http://microtec.eu/assets/products/goldeneye300/Midrotec-Goldeneye-300-1.pdf, 4 pages.

* cited by examiner

DETECTOR ASSEMBLIES AND METHODS FOR HELICAL CT SCANNING

BACKGROUND

The embodiments described herein relate generally to image reconstruction systems, and more particularly, to detector assemblies for helical CT scanning.

In some computed tomography (CT) imaging system configurations, an x-ray source projects a fan-shaped beam which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile and reconstruct an image of the object.

At least some known CT systems require a contiguous two-dimensional detector array to achieve high throughput for helical scanning. Detectors are generally the most expensive part of a CT system (either measured by unit area or channel count). It is also generally desirable to increase the throughput of a CT system to process more articles per hour in order to reduce operational costs of the system. As such, there is a general need to increase the size of the detector. However, increasing the area and channel count of a detector is relatively expensive. Accordingly, it would be desirable to increase throughput of a helical CT scanner without increasing the number of detector elements.

BRIEF SUMMARY

In one aspect, a helical CT scanner for imaging an object is provided. The helical CT scanner includes an X-ray emitter configured to emit X-ray beams towards the object, and a detector array positioned opposite the X-ray emitter, the detector array including a plurality of discrete detector blocks arranged in a two-dimensional grid, each detector block including a plurality of pixels, wherein at least one first gap is defined between adjacent detector blocks in a first direction, and wherein at least one second gap is defined between adjacent detector blocks in a second direction. The helical CT scanner further includes a processing device communicatively coupled to said detector array, said processing device configured to reconstruct an image of the object based on image data acquired using said detector array.

In another aspect, a method for imaging an object is provided. The method includes positioning the object between an X-ray emitter and a detector array, the detector array including a plurality of discrete detector blocks arranged in a two-dimensional grid, each detector block including a plurality of pixels, wherein at least one first gap is defined between adjacent detector blocks in a first direction, and wherein at least one second gap is defined between adjacent detector blocks in a second direction, acquiring image data from the detector array using a processing device communicatively coupled to the detector array, and reconstructing, using the processing device, an image of the object based on the acquired image data.

In yet another aspect, a detector array for a helical CT scanner is provided. The detector array includes a plurality of discrete detector blocks arranged in a two-dimensional grid on said substrate, each detector block comprising a plurality of pixels, wherein at least one first gap is defined between adjacent detector blocks in a first direction, and wherein at least one second gap is defined between adjacent detector blocks in a second direction.

DETAILED DESCRIPTION

The systems and methods described herein provide a detector array include a plurality of discrete detector blocks. The detector blocks are arranged in a two-dimensional grid on a substrate. Gaps are defined between adjacent detector blocks. The gaps between detector blocks do not interfere with image quality, and enable the detector array to increase throughput without increasing the number of detector elements.

Figure 1:
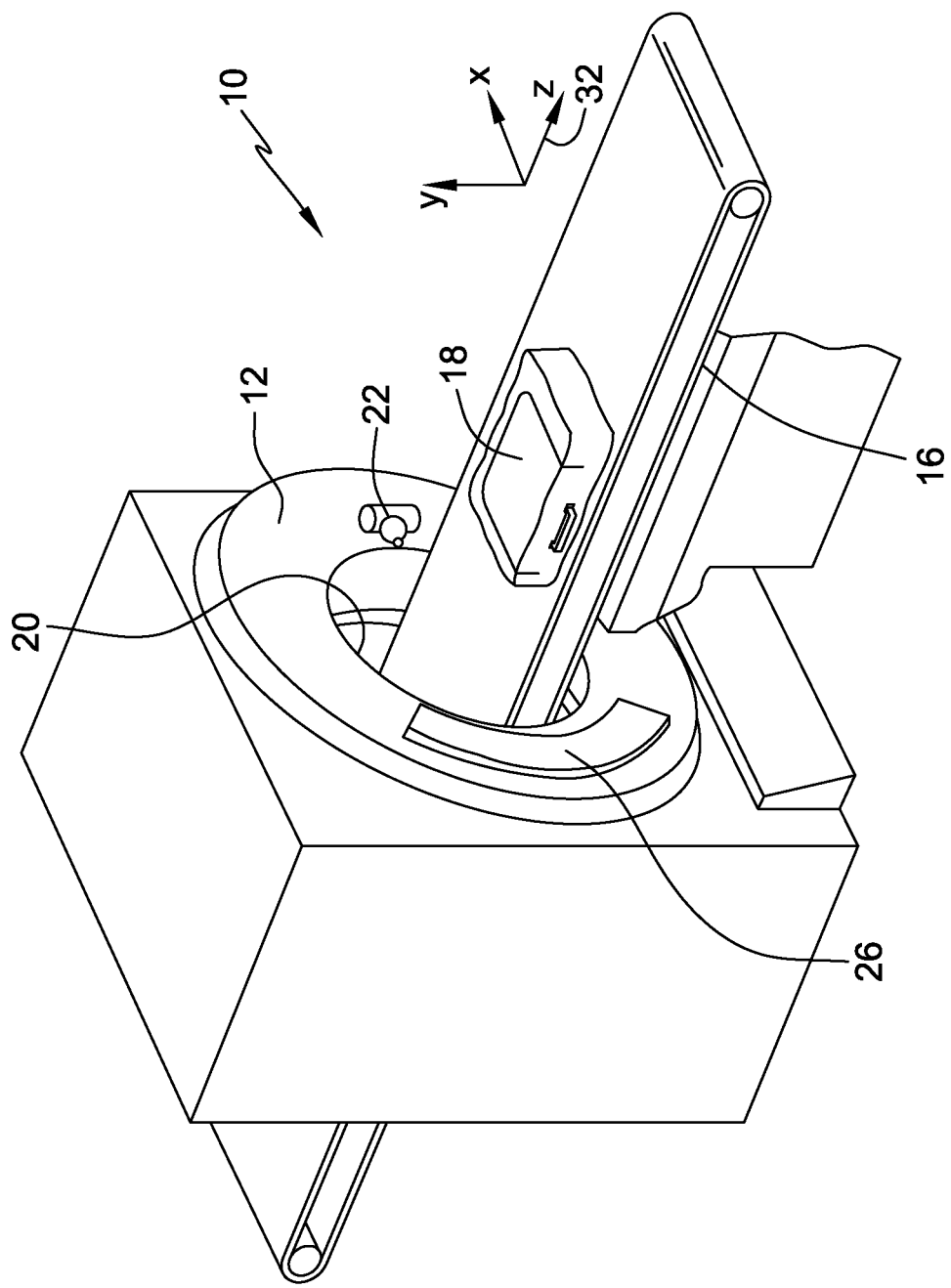
FIG. 1 is a perspective view of an exemplary CT imaging system.
Figure 2:
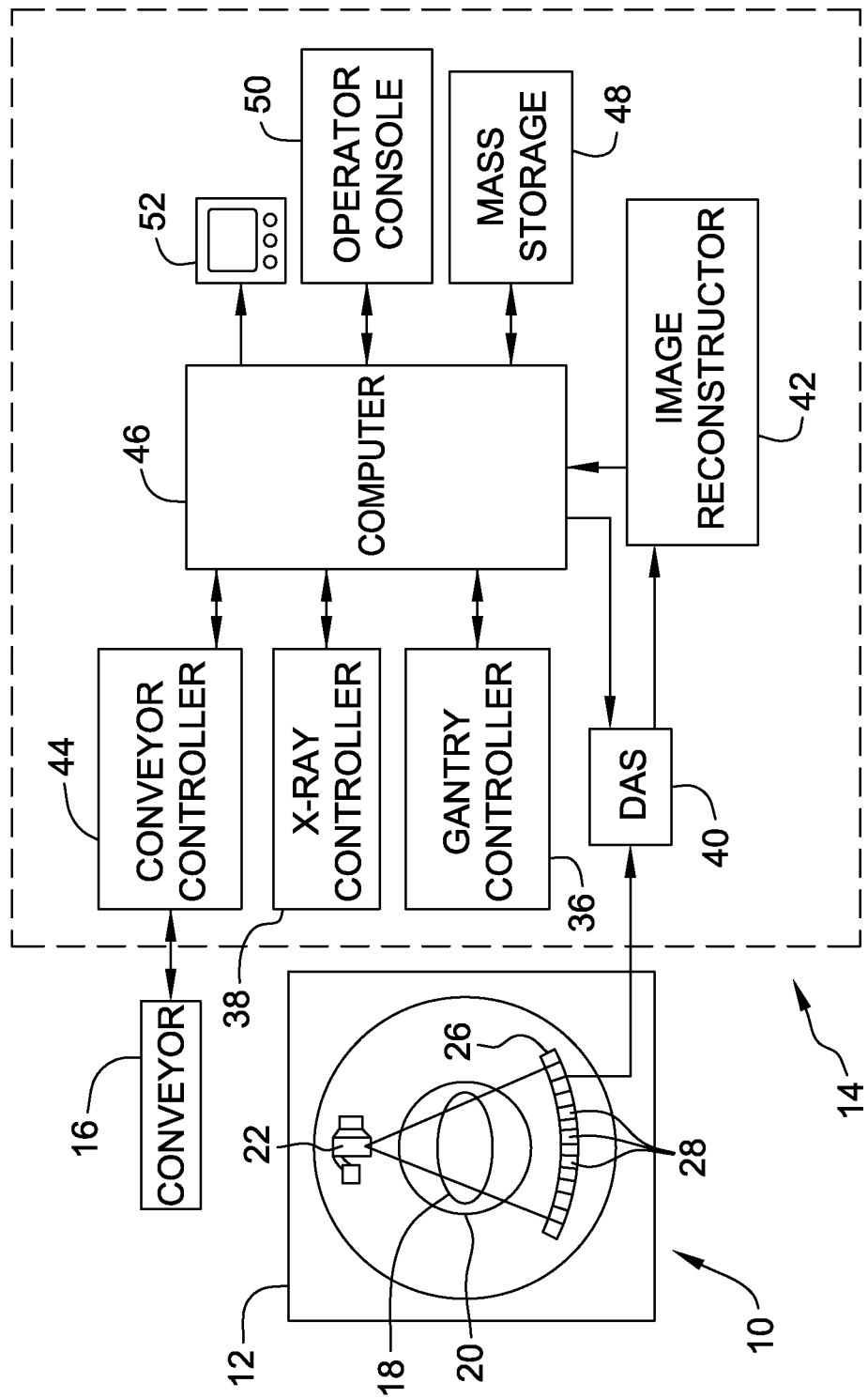
FIG. 2 is a schematic diagram of the CT imaging system shown in FIG. 1.

Referring now to FIGS. 1 and 2, a computed tomography (CT) imaging system 10 is shown. CT imaging system 10 is shown having a gantry 12, which is representative of a CT scanner, a control system 14, and a motorized conveyor belt 16 for positioning an object 18, such as a piece of luggage, in a gantry opening 20 defined through gantry 12. Gantry 12 includes an x-ray source 22 that projects a fan beam of x-rays 24 toward a detector array 26 on the opposite side of gantry 12. Detector array 26 is formed by detector elements 28, which are radiation detectors that each produce a signal having a magnitude that represents and is dependent on the intensity of the attenuated x-ray beam after it has passed through object 18 being imaged. During a helical scan that acquires x-ray projection data, gantry 12 along with the x-ray source 22 and detector array 26 rotate within an x-y plane and around object 18 about a center of rotation, while object 18 is moved through gantry 12 in a z-direction 32 perpendicular to the x-y plane of rotation. In the exemplary embodiment, detector array 26 includes a plurality of detector rings each having a plurality of detector elements 28, the detector rings having an angular configuration corresponding to x-ray source 22.

Gantry 12 and x-ray source 22 are controlled by control system 14, which includes a gantry controller 36, an x-ray controller 38, a data acquisition system (DAS) 40, an image reconstructor 42, a conveyor controller 44, a computer 46, a mass storage-system 48, an operator console 50, and a display device 52. Gantry controller 36 controls the rotational speed and position of gantry 12, while x-ray controller 38 provides power and timing signals to x-ray source 22, and data acquisition system 40 acquires analog data from detector elements 28 and converts the data to digital form for subsequent processing. Image reconstructor 42 receives the digitized x-ray data from data acquisition system 40 and performs an image reconstruction process that involves filtering the projection data using a helical reconstruction algorithm.

Computer 46 is in communication with the gantry controller 36, x-ray controller 38, and conveyor controller 44 whereby control signals are sent from computer 46 to controllers 36, 38, 44 and information is received from controllers 36, 38, 44 by computer 46. Computer 46 also provides commands and operational parameters to data acquisition system 40 and receives reconstructed image data from image reconstructor 42. The reconstructed image data is stored by computer 46 in mass storage system 48 for subsequent retrieval. An operator interfaces with computer 46 through operator console 50, which may include, for example, a keyboard and a graphical pointing device, and receives output, such as, for example, a reconstructed image, control settings and other information, on display device 52.

Communication between the various system elements of FIG. 2 is depicted by arrowhead lines, which illustrate a means for either signal communication or mechanical operation, depending on the system element involved. Communication amongst and between the various system elements may be obtained through a hardwired or a wireless arrangement. Computer 46 may be a standalone computer or a network computer and may include instructions in a variety of computer languages for use on a variety of computer platforms and under a variety of operating systems. Other examples of computer 46 include a system having a microprocessor, microcontroller or other equivalent processing device capable of executing commands of computer readable data or program for executing a control algorithm. In order to perform the prescribed functions and desired processing, as well as the computations therefore (e.g., the execution of filtered back projection, fourier analysis algorithm(s), the control processes prescribed herein, and the like), computer 46 may include, but not be limited to, a processor(s), memory, storage, register(s), timing, interrupt(s), communication interfaces, and input/output signal interfaces, as well as combinations including at least one of the foregoing. For example, computer 46 may include input signal filtering to enable accurate sampling and conversion or acquisitions of such signals from communications interfaces. As described above, exemplary embodiments can be implemented through computer-implemented processes and apparatuses for practicing those processes.

Figure 3:
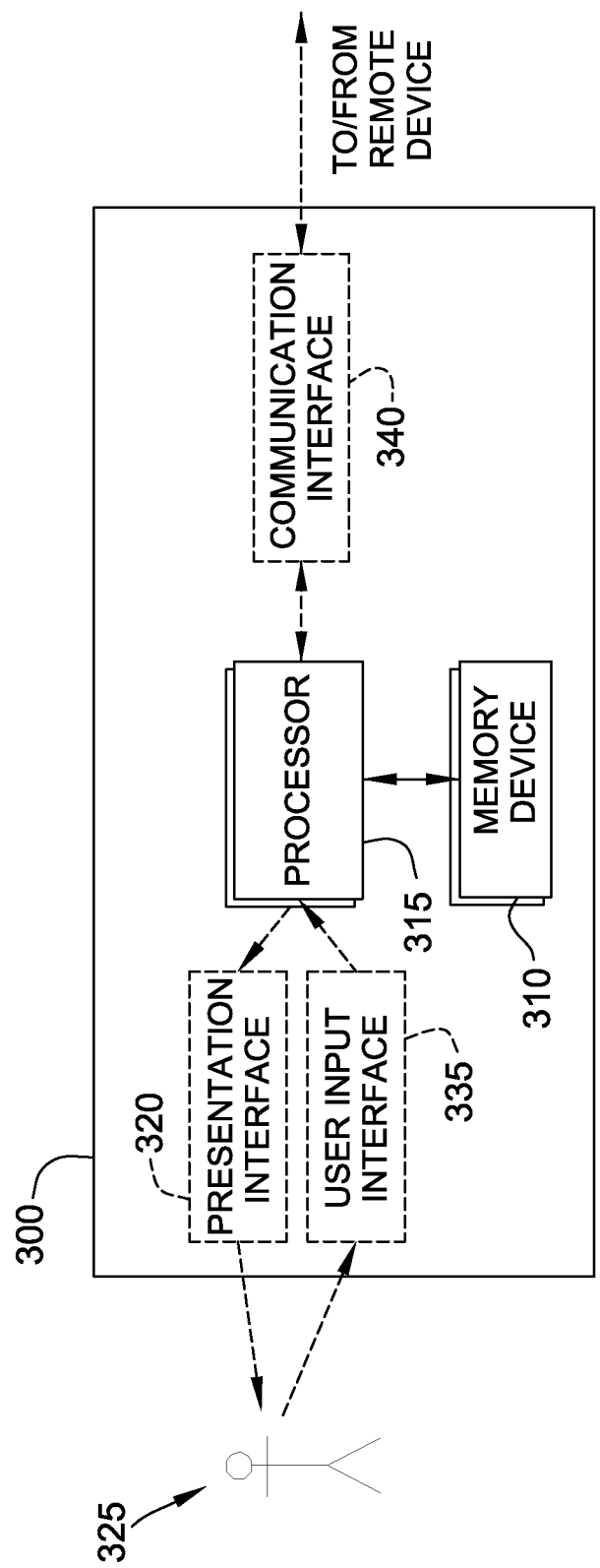
FIG. 3 is a block diagram of an exemplary computing device that may be used with the CT imaging system shown in FIGS. 1-3.

FIG. 3 is a block diagram of a computing device 300 that may be used to reconstruct an image of object 18, as described herein. Computing device 300 may be implemented as part of control system 14 or may be a separate computing device in communication with CT imaging system 10 or another imaging system. Computing device 300 includes at least one memory device 310 and a processor 315 that is coupled to memory device 310 for executing instructions. In some embodiments, executable instructions are stored in memory device 310. In the exemplary embodiment, computing device 300 performs one or more operations described herein by programming processor 315. For example, processor 315 may be programmed by encoding an operation as one or more executable instructions and by providing the executable instructions in memory device 310.

Processor 315 may include one or more processing units (e.g., in a multi-core configuration). Further, processor 315 may be implemented using one or more heterogeneous processor systems in which a main processor is present with secondary processors on a single chip. In another illustrative example, processor 315 may be a symmetric multi-processor system containing multiple processors of the same type. Further, processor 315 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), graphics processing units (GPU), and any other circuit capable of executing the functions described herein.

In the exemplary embodiment, memory device 310 is one or more devices that enable information such as executable instructions and/or other data to be stored and retrieved. Memory device 310 may include one or more computer readable media, such as, without limitation, dynamic random access memory (DRAM), static random access memory (SRAM), a solid state disk, and/or a hard disk. Memory device 310 may be configured to store, without limitation, application source code, application object code, source code portions of interest, object code portions of interest, configuration data, execution events and/or any other type of data. Further, reference templates may be stored on memory device 310.

In the exemplary embodiment, computing device 300 includes a presentation interface 320 that is coupled to processor 315. Presentation interface 320 presents information to a user 325. For example, presentation interface 320 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 320 includes one or more display devices.

In the exemplary embodiment, computing device 300 includes a user input interface 335. User input interface 335 is coupled to processor 315 and receives input from user 325. User input interface 335 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 320 and user input interface 335.

Computing device 300, in the exemplary embodiment, includes a communication interface 340 coupled to processor 315. Communication interface 340 communicates with one or more remote devices (e.g., in some embodiments, CT imaging system 10). To communicate with remote devices, communication interface 340 may include, for example, a wired network adapter, a wireless network adapter, and/or a mobile telecommunications adapter.

Figure 4:
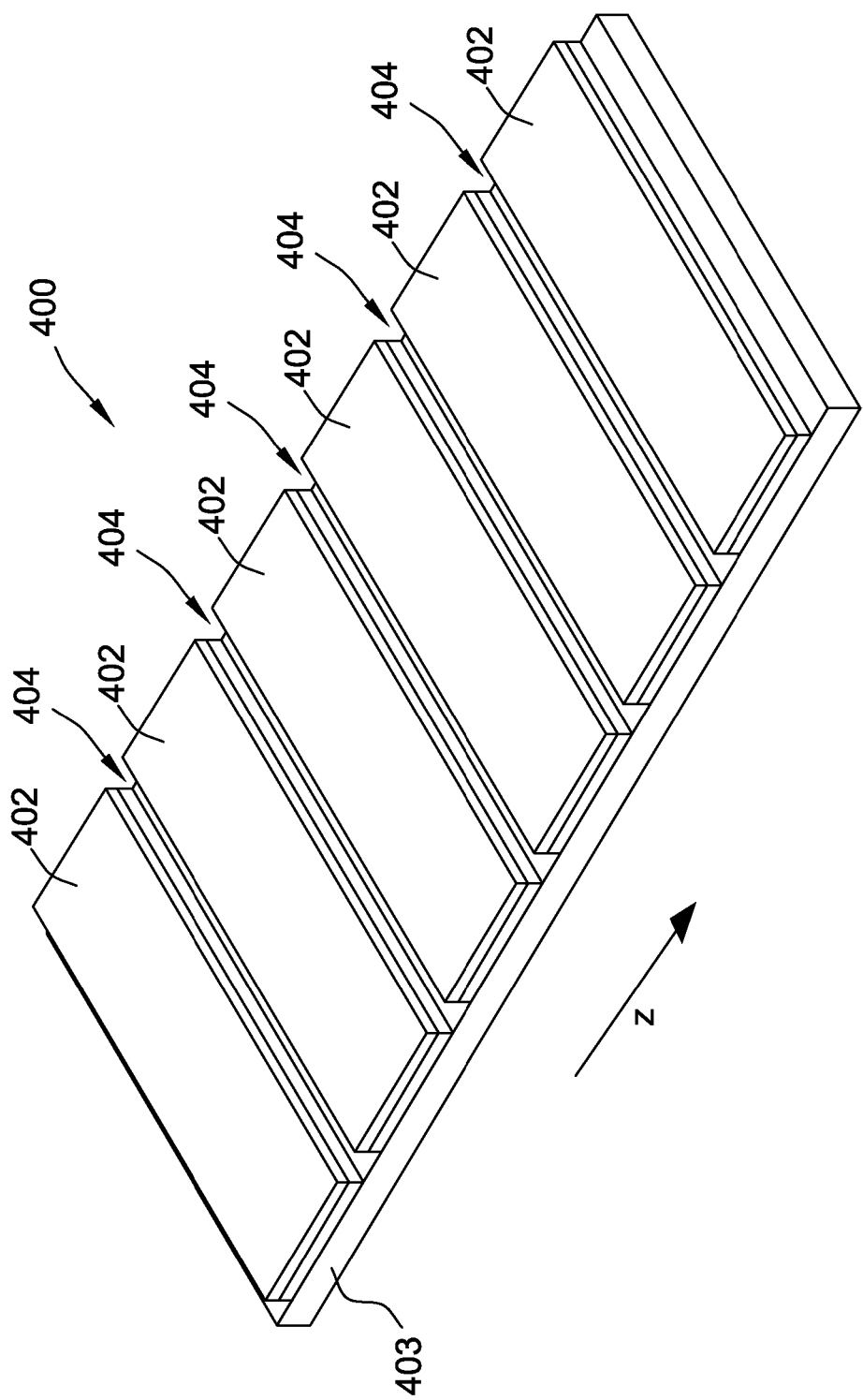
FIG. 4 is a schematic diagram of an exemplary detector array portion that may be used with the CT imaging system shown in FIGS. 1 and 2.

FIG. 4 is a schematic diagram of an exemplary detector array portion 400. For example, portion 400 may form a part of detector array 26 (shown in FIGS. 1 and 2). Portion 400 includes a plurality of detector blocks 402 mounted to a substrate 403. In the exemplary embodiment, portion 400 includes six detector blocks 402. Alternatively, portion 400 may include any number of detector blocks that enables portion 400 to function as described herein.

Each detector block 402 is segmented into a plurality of pixels (i.e., discrete detector elements). Specifically, each detector block 402 includes a two-dimensional array of pixels. In the exemplary embodiment, each detector block 402 includes eight columns and thirty-two rows of pixels, for a total of two-hundred fifty-six pixels. Alternatively, each detector block 402 may include any suitable number of pixels in any suitable arrangement.

As shown in FIG. 4, gaps 404 are defined between adjacent detector blocks 402. In the exemplary embodiment, gaps 404 are empty (i.e., filled with air). Alternatively, gaps 404 may be filled with one or more materials. For example, gaps 404 may contain foam, structural materials, and/or x-ray shielding material. In embodiments where gaps 404 are filled, the filling material is generally relatively inexpensive, as compared to active pixels. In the example embodiment, gaps 404 have a width approximately equal to a multiple of a pixel size in detector blocks 402. For example, gaps 404 may be approximately 1, 2, 3, etc. pixels wide. Alternatively, gaps 404 may have any width that enables detector array portion 400 to function as described herein. For example, gaps 404 may have a width that is a fraction of a multiple of the pixel size (e.g., 1½ pixels wide). Further, in some embodiments, different gaps 404 may have a different size. For example, the centermost gap 404 relative to the z-direction may be relatively small, with gaps towards the z-extrema being relatively larger, where acquired image data is less useful.

Figure 5:
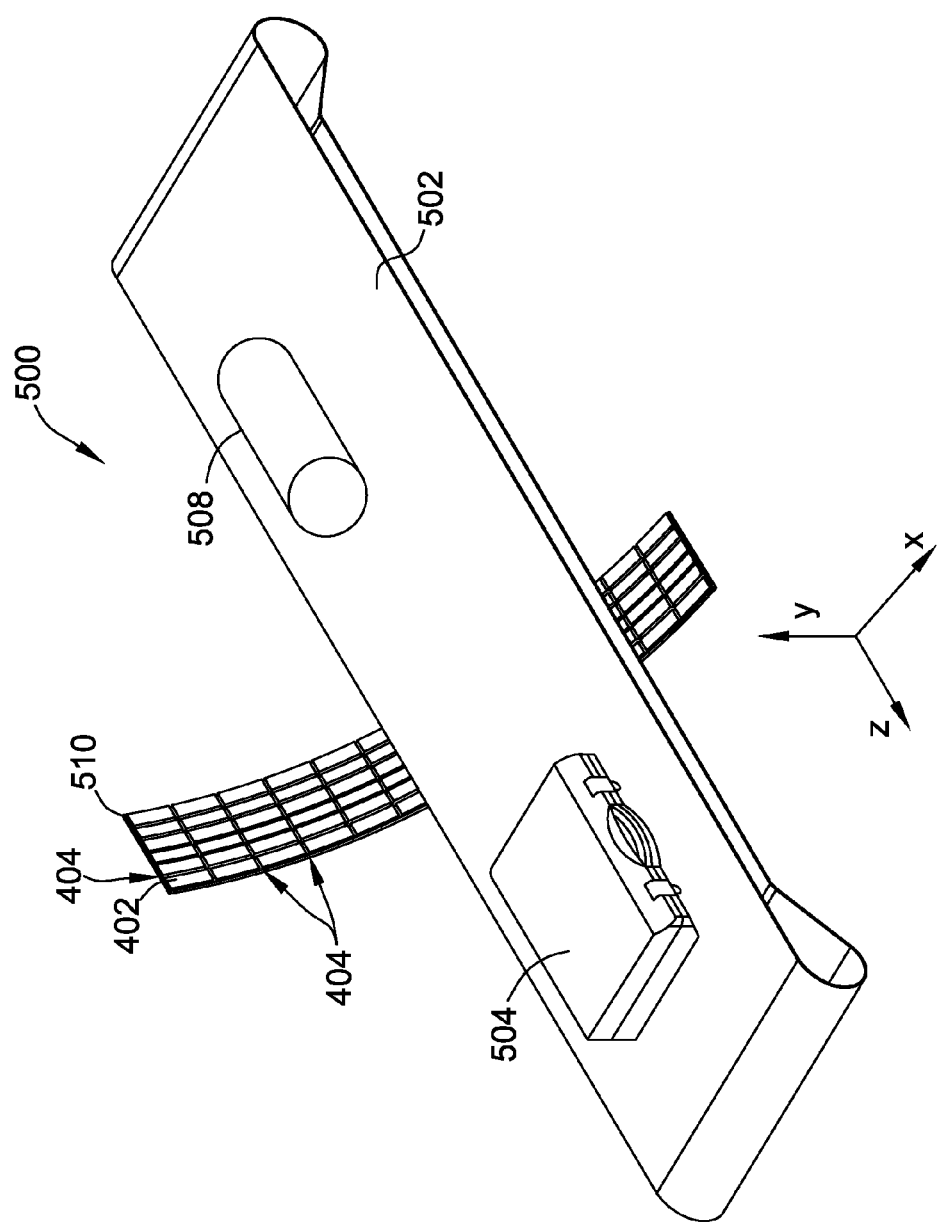
FIG. 5 is a perspective partial view of an exemplary CT imaging system.

FIG. 5 is a perspective partial view of a CT imaging system 500, such as CT imaging system 10 (shown in FIGS. 1 and 2). For clarity, several components of CT imaging system 500 are not shown in FIG. 5. CT imaging system 500 includes a conveyor 502 that moves an object 504 along the z-direction. CT imaging system 500 also includes an x-ray source 508, such as x-ray source 22 (shown in FIGS. 1 and 2), and a detector array 510, such as detector array 26 (shown in FIGS. 1 and 2).

Detector array 510 includes portion 400 in the exemplary embodiment. Specifically, detector array 510 includes a plurality of rows and columns of detector blocks 402 arranged on substrate 403. As shown in FIG. 5, substrate 403 is substantially arcuate. In the exemplary embodiment, detector array 510 includes detector blocks 402 arranged in a two-dimensional grid of six columns and twelve rows, for a total of seventy-two detector blocks 402. Alternatively, detector array 510 may include any number and arrangement of detector blocks 402 that enables detector array 510 to function as described herein.

In the exemplary embodiment, gaps 404 are defined between adjacent detector blocks 402. For example, each row of detector blocks 402 includes five such gaps 404 (i.e., gaps 404 between detector blocks 402 adjacent one another in a first direction), and each column of detector blocks 402 includes eleven such gaps 404 (i.e., gaps 404 between detector blocks 402 adjacent one another in a second direction). Gaps 404 enable detector array 510 to have a relatively large overall surface area, without requiring the entire surface area to be occupied by detector elements.

When reconstructing an image of object 504, an image reconstruction system, such as computing device 300 (shown in FIG. 3) takes gaps 404 into account. For example, in some embodiments, the image reconstruction system may generate interpolated image data corresponding to gaps 404 from image data acquired at detector blocks 402, and generate a reconstructed image from the interpolated image data and the acquired image data. Alternatively, image reconstruction algorithms used by the image reconstruction system may be modified to generate a reconstructed image from the acquired image data alone (i.e., without generating interpolated image data for gaps 404).

The embodiments described herein provide a detector array include a plurality of discrete detector blocks. The detector blocks are arranged in a two-dimensional grid on a substrate. Gaps are defined between each adjacent detector blocks. The gaps between detector blocks do not interfere with image quality, and enable the detector array to increase throughput without increasing the number of detector elements.

The systems and methods described herein may be used to detect contraband. As used herein, the term "contraband" refers to illegal substances, explosives, narcotics, weapons, special nuclear materials, dirty bombs, nuclear threat materials, a threat object, and/or any other material that a person is not allowed to possess in a restricted area, such as an airport. Contraband may be hidden within a subject (e.g., in a body cavity of a subject) and/or on a subject (e.g., under the clothing of a subject). Contraband may also include objects that can be carried in exempt or licensed quantities intended to be used outside of safe operational practices, such as the construction of dispersive radiation devices.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Exemplary embodiments of methods and systems are described above in detail. The methods and systems are not limited to the specific embodiments described herein, but rather, components of systems and/or steps of the methods may be used independently and separately from other components and/or steps described herein. Accordingly, the exemplary embodiment can be implemented and used in connection with many other applications not specifically described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A helical CT scanner for imaging an object as the object moves through said helical CT scanner in a z-direction, said helical CT scanner comprising:
   an X-ray emitter configured to emit X-ray beams towards the object;

a detector array positioned opposite said X-ray emitter and rotatable about an axis parallel to the z-direction, said detector array comprising:
a plurality of discrete detector blocks arranged in a two-dimensional grid, each detector block comprising a plurality of pixels, wherein at least one first gap is defined between adjacent detector blocks in a first direction corresponding to the z-direction, and wherein at least one second gap is defined between adjacent detector blocks in a second direction; and
a processing device communicatively coupled to said detector array, said processing device configured to reconstruct an image of the object based on image data acquired using said detector array.

2. A helical CT scanner in accordance with claim 1, wherein the at least one first gap includes a plurality of first gaps, the plurality of first zaps including a centermost first gap relative to the z-direction, the centermost first gap having a width smaller than a width of at least one other first gap of the plurality of first gaps.

3. A helical CT scanner in accordance with claim 1, wherein the at least one first gap and the at least one second gap are filled with an x-ray shielding material.

4. A helical CT scanner in accordance with claim 1, wherein each first gap and each second gap has a width approximately equal to a multiple of a width of a pixel in said detector block.

5. A helical CT scanner in accordance with claim 1, wherein said processing device is further configured to generate interpolated image data corresponding to the first and second gaps based on the acquired image data.

6. A helical CT scanner in accordance with claim 5, wherein to reconstruct an image of the object, said processing device is configured to reconstruct the image based on the acquired image data and the interpolated image data.

7. A helical CT scanner in accordance with claim 1, wherein to reconstruct an image of the object, said processing device is configured to reconstruct the image based on the acquired image data without using interpolated image data.

8. A helical CT scanner in accordance with claim 1, further comprising a substantially arcuate substrate, wherein said plurality of discrete detector blocks are arranged on the substrate.

9. A method for imaging an object as the object moves through a gantry in a z-direction, said method comprising:
positioning the object between an X-ray emitter and a detector array of the gantry, the detector array rotatable about an axis parallel to the z-direction and including a plurality of discrete detector blocks arranged in a two-dimensional grid, each detector block including a plurality of pixels, wherein at least one first gap is defined between adjacent detector blocks in a first direction corresponding to the z-direction, and wherein at least one second gap is defined between adjacent detector blocks in a second direction;
acquiring image data from the detector array using a processing device communicatively coupled to the detector array; and
reconstructing, using the processing device, an image of the object based on the acquired image data.

10. A method in accordance with claim 9, wherein positioning the object comprises positioning the object between an X-ray emitter and a detector array that includes detector blocks each having two-hundred fifty-six pixels.

11. A method in accordance with claim 9, wherein positioning the object comprises positioning the object between an X-ray emitter and a detector array that includes six columns and twelve rows of detector blocks.

12. A method in accordance with claim 9, wherein positioning the object comprises positioning the object between an X-ray emitter and a detector array that includes first and second gaps each having a width approximately equal to a multiple of a width of a pixel in said detector block.

13. A method in accordance with claim 9, further comprising, generating, using the processing device, interpolated image data corresponding to the first and second gaps based on the acquired image data.

14. A method in accordance with claim 13, wherein reconstructing an image of the object comprises reconstructing the image based on the acquired image data and the interpolated image data.

15. A method in accordance with claim 9, wherein reconstructing an image of the object comprises reconstructing the image based on the acquired image data without using interpolated image data.

16. A method in accordance with claim 9, wherein positioning the object comprises positioning the object between an X-ray emitter and a detector array that includes a plurality of discrete detector blocks arranged on a substantially arcuate substrate.

17. A detector array for a helical CT scanner configured to image an object as the object moves through the helical CT scanner in a z-direction, said detector array rotatable about an axis parallel to the z-direction, said detector array comprising a plurality of discrete detector blocks arranged in a two-dimensional grid on a substrate, each detector block comprising a plurality of pixels, wherein at least one first gap is defined between adjacent detector blocks in a first direction corresponding to the z-direction, and wherein at least one second gap is defined between adjacent detector blocks in a second direction.

18. A detector array in accordance with claim 17, wherein each detector block comprises two-hundred fifty-six pixels.

19. A detector array in accordance with claim 17, wherein said detector array comprises six columns and twelve rows of detector blocks.

20. A detector array in accordance with claim 17, wherein each first and second gap has a width approximately equal to a multiple of a width of a pixel in said detector block.

* * * * *